(12) United States Patent
Muellinger et al.

(10) Patent No.: US 10,857,310 B2
(45) Date of Patent: Dec. 8, 2020

(54) MIXING CHANNEL FOR AN INHALATION DEVICE AND INHALATION DEVICE

(71) Applicant: VECTURA GMBH, Gauting (DE)

(72) Inventors: Bernhard Muellinger, Munich (DE); Martin Huber, Furstenfeldbruck (DE); Tobias Kolb, Neuried (DE); Monika Hartmann, Kaufering (DE)

(73) Assignee: VECTURA GMBH, Gauting (DE)

( * ) Notice: Subject to any disclaimer, the term of this patent is extended or adjusted under 35 U.S.C. 154(b) by 1106 days.

(21) Appl. No.: 14/382,392

(22) PCT Filed: Mar. 8, 2013

(86) PCT No.: PCT/EP2013/054705
§ 371 (c)(1),
(2) Date: Sep. 2, 2014

(87) PCT Pub. No.: WO2013/132056
PCT Pub. Date: Sep. 12, 2013

(65) Prior Publication Data
US 2015/0174343 A1     Jun. 25, 2015

(30) Foreign Application Priority Data

Mar. 9, 2012 (EP) .................................... 12158852
Oct. 26, 2012 (EP) .................................... 12190139

(51) Int. Cl.
*A61M 11/00*        (2006.01)
*A61M 15/00*        (2006.01)
(Continued)

(52) U.S. Cl.
CPC ......... *A61M 11/003* (2014.02); *A61M 11/005* (2013.01); *A61M 11/02* (2013.01);
(Continued)

(58) Field of Classification Search
CPC .. A61M 11/003; A61M 11/02; A61M 11/005; A61M 15/0021; A61M 15/00;
(Continued)

(56) References Cited

U.S. PATENT DOCUMENTS 4,592,348 A * 6/1986 Waters, IV ....... A61M 15/0091
                                                    128/200.23
4,976,259 A    12/1990 Higson et al.
(Continued)

FOREIGN PATENT DOCUMENTS

CN       101155608 A      4/2008
DE       102005010965      8/2006
(Continued)

OTHER PUBLICATIONS

Office Action dated Jan. 20, 2020 in Chinese Application No. 201711318505.2.

*Primary Examiner* — Kendra D Carter
*Assistant Examiner* — Victoria Murphy
(74) *Attorney, Agent, or Firm* — Reed Smith LLP (57) ABSTRACT

The invention relates to a mixing channel for an inhalation device, and in particular to a mixing channel with improved injection and mixing properties for injecting and mixing a liquid drug into an air flow streaming in the mixing channel, thereby producing an aerosol to be inhaled by a patient. One aspect of the invention relates to a mixing channel for an inhalation device, comprising an inlet opening, an outlet opening, and an injection zone located between the inlet opening and the outlet opening, wherein the injection zone has a longitudinal center axis, wherein the injection zone comprises (a) a built-in nebulizer, or (b) a detachable nebulizer, or (c) a member adapted to receive a detachable nebulizer, wherein the effective cross sectional area of the mixing channel in a plane perpendicular to the longitudinal
(Continued)

center axis is smaller in the injection zone than upstream of the injection zone.

26 Claims, 7 Drawing Sheets (51) Int. Cl.
    *A61M 11/06* (2006.01)
    *A61M 15/06* (2006.01)
    *A61M 11/02* (2006.01)

(52) U.S. Cl.
    CPC ............ *A61M 11/06* (2013.01); *A61M 15/00* (2013.01); *A61M 15/009* (2013.01); *A61M 15/0021* (2014.02); *A61M 15/0086* (2013.01); *A61M 15/06* (2013.01); *A61M 2205/75* (2013.01); *A61M 2206/10* (2013.01)

(58) Field of Classification Search
    CPC .............. A61M 15/0086; A61M 15/06; A61M 15/009; A61M 11/06; A61M 2205/75; A61M 2206/10
    See application file for complete search history.

(56) References Cited

U.S. PATENT DOCUMENTS

| | | | |
|---|---|---|---|
| 5,040,527 A * | 8/1991 | Larson | A61M 15/00 128/200.14 |
| 5,178,138 A * | 1/1993 | Walstrom | A61M 15/0086 128/200.14 |
| 5,522,380 A | 6/1996 | Dwork | |
| 5,839,430 A * | 11/1998 | Cama | A61B 5/0871 128/200.14 |
| 7,600,511 B2 * | 10/2009 | Power | A61M 15/0085 128/200.14 |
| 2004/0089295 A1 | 5/2004 | Gallem et al. | |
| 2005/0133025 A1 * | 6/2005 | Laiho | A61M 15/0045 128/200.23 |
| 2005/0229926 A1 | 10/2005 | Fink et al. | |
| 2005/0252509 A1 | 11/2005 | Rustad et al. | |
| 2006/0054166 A1 | 3/2006 | Knoch et al. | |
| 2008/0202506 A1 | 8/2008 | Mahoney et al. | |
| 2009/0211577 A1 * | 8/2009 | Eistetter | A61P 33/02 128/203.15 |
| 2010/0282247 A1 | 11/2010 | Kadrichu et al. | |
| 2012/0037154 A1 | 2/2012 | Gallem et al. | |

FOREIGN PATENT DOCUMENTS

| | | | |
|---|---|---|---|
| JP | 08071152 | 3/1996 | |
| JP | 2005510309 | 4/2005 | |
| JP | 2008515606 | 5/2008 | |
| RU | 2179075 | 2/2002 | |
| WO | 1997012687 | 4/1997 | |
| WO | 2003095009 | 11/2003 | |
| WO | 2006083014 | 8/2006 | |
| WO | 2006105980 | 10/2006 | |
| WO | 2007116953 | 10/2007 | |
| WO | 2008016156 | 2/2008 | |
| WO | 2008050542 | 5/2008 | |
| WO | 2008058941 | 5/2008 | |
| WO | 2009136654 | 11/2009 | |
| WO | 2010065616 | 6/2010 | |
| WO | WO-2010149280 A1 * | 12/2010 | ............... A61D 7/04 |
| WO | 2011163272 | 12/2011 | |

* cited by examiner

Prior Art

MIXING CHANNEL FOR AN INHALATION DEVICE AND INHALATION DEVICE

RELATED APPLICATIONS

This application is the United States national stage of International Application No. PCT/EP2013/054705, filed Mar. 8, 2013, which was published as International Publication No. WO 2013/132056 A1, and which claims benefit of European Application No. 12158852.9 filed, Mar. 9, 2012 and European Application No. 12190139.1 filed Oct. 26, 2012. All applications are incorporated by reference in their entirety herewith.

The invention relates to a mixing channel for an inhalation device, and in particular to a mixing channel with improved injection and mixing properties for injecting and mixing liquid droplets of a drug formulation into an air flow streaming in the mixing channel, thereby producing an aerosol to be inhaled by a patient.

There are various medical applications for inhalation devices allowing a patient to inhale an aerosol, e.g., the treatment of asthma, cystic fibrosis, and a number of other respiratory diseases. An aerosol is a dispersion of small solid particles or liquid droplets in a continuous gas phase. For medical inhalation treatment, it is usually required to provide an aerosol with fine droplets of a liquid formulation of a bioactive agent or drug, e.g. an aqueous solution of the drug and suitable excipients. Since, in the ideal case, the droplets of the liquid formulation comprising said medical agent should reach even the smallest branches of the lungs, it is particularly desirable to provide an aerosol with the droplets being equally and homogeneously distributed in the gas. Therefore, the liquid formulation of a bioactive agent or drug is often atomised by means of a nebulizer; i.e., an aerosol generator capable of converting a liquid into a respirable aerosol in a continuous manner.

It is noted that inhalation devices comprising nebulizers as aerosol generator are sometimes also referred to as nebulizers. Consequently, it is the context which determines whether the expression "nebulizer" should be interpreted so as to refer to the aerosol generator only or the complete inhalation device.

As defined herein, common nebulizers are, for instance, ultrasonic nebulizers, jet nebulizers and vibrating mesh nebulizers. These devices operate continuously over the course of a few breaths up to about 45 min (or longer if the patient requires breaks during an inhalation treatment). During this time, they emit aerosol either constantly or in pulses which are adapted to the user's breathing pattern; e.g., triggered by the onset of inhalation.

Further inhalation devices capable of dispersing small droplets of liquid drug formulation in air are, for example, pressurized metered dose inhalers, soft mist inhalers (such as Respimat® by Boehringer Ingelheim) and other aerosol generators with micro-machined silicon chip-type spray nozzles. These inhalation devices are not commonly considered to represent nebulizers, because they are designed (e.g., by the use of tension springs) to deliver, upon actuation, only a single pulse of aerosolised liquid. Therefore, if more than one breath was required to administer a desired dose, repeated manual actuations would be necessary when using e.g. pressurized metered dose inhalers and/or soft mist inhalers. Moreover, pressurised metered dose inhalers generate aerosol from pressurised liquids comprising propellants, whereas nebulizers generate aerosols from unpressurised liquid containing no propellants.

In order to ensure reproducible drug administration to the lungs, with regard to the dose as well as the region of deposition within the lungs, it is vital that the droplets of aerosolised liquid formulation are as monodisperse as possible and homogeneously distributed in the gas phase. Coalescence of droplets and/or impaction with the inner walls of the inhalation device (or the patient's mouth) would result in losses of drug formulation and irreproducible dosing and deposition. Thus, sufficient mixing of the nascent aerosol with the patient's inhalation air flow streaming through the inhalation device is required, as well as optimized flow properties of the "diluted" aerosol on its way from the inhalation device into the patient's mouth and lungs.

With vibrating mesh nebulizers or ultrasonic nebulizers, the nascent aerosol is typically rather dense, with an output rate sometimes being in the region of about 1 ml aerosol per minute. Hence, avoiding droplet coalescence and impaction at the inner walls, for instance, of the vibrating mesh inhaler is more challenging than with other inhalation devices such as the traditional jet nebulizers with typical output rates of about 0.3 to 0.4 ml/min.

Currently available vibrating mesh nebulizers, for instance, typically comprise a liquid reservoir, an aerosol generator comprising the vibrating membrane (or vibrating mesh) and a mouthpiece. These components are typically assembled so that the nebulizer membrane is either arranged approximately vertical or horizontal.

The benefit of horizontally arranged nebulizer membranes is that they allow for an easy, gravity-driven and thus less variable flow of the liquid from a reservoir positioned above said membrane. However, the nascent aerosol is then introduced into the air flow channel from the top and mostly perpendicular to it, so that typically mixing chambers are required in order to avoid particle collision with each other and/or the device's inner walls and to homogeneously mix and slow down the aerosolized droplets within the inspiratory air flow before inhalation by the user. Unfortunately, these mixing chambers are rather spacious and increase the dimensions of such inhalation devices unfavourably. Furthermore, owing to longer residence times of the aerosol in the mixing chamber and potential turbulences within said mixing chamber, sedimentation and impaction of the aerosolized droplets may occur; increasing wastage of the aerosolized formulation and decreasing dose reproducibility. Also, such vertically stacked arrangements of liquid reservoir, aerosol generator (with horizontal membrane) and mixing chamber leads to devices which are rather high compared to their width. This could lead to handling problems; e.g., devices may tilt, especially upon filling of the reservoir or in filled state.

With vertically arranged membranes, on the other hand, the nascent aerosol can be introduced horizontally into the airflow channel, and the aerosol generator can be positioned at an angle to the direction of the air flow without changing the vertical arrangement of the membrane. Depending on the selected angle between the aerosol generator and the air flow channel, it is possible to introduce the aerosol roughly in parallel or even completely in parallel with the direction of the air flow. This approach is, for example, chosen in WO 2009/135871 A1. However, since the liquid has to be supplied to a vertically positioned nebulizer membrane (rather than simply flowing onto it as it does with horizontal membranes), even minor handling deviations, such as tilting the device during inhalation, can lead to distinct variations in liquid supply and aerosol output. Also, the residual volume remaining in the liquid reservoir at the end of the inhalation treatment is typically higher than for inhalation devices with horizontally arranged membranes.

Another approach, as described in DE 10 2005 029 498 B4, is the use of an annular air stream surrounding the aerosol generator and/or the nascent aerosol, so that the aerosol plume is engulfed in an "air jacket" to avoid particle collision with the inner walls of the mouthpiece. This often has practical limitations. It increases the dimensions of the device unfavourably, because the aerosol cone broadens quickly once emitted from the membrane. Beyond that, the annular ring slit has to be comparatively large in order to not create turbulences. In addition, inhalation devices using the "air jacket" approach require more components.

An approach slightly similar to said "air jacket" is the use of air slits in the mouthpiece through which ambient air is drawn by reduced pressure when the aerosol is passing the mouthpiece at high speed. Such air slits are, for example, provided with the Respimat® soft mist inhaler. While requiring far less space and no extra components than the above mentioned annular ring slits, the air slits in the mouthpiece are also less efficient and cannot prevent droplet deposition within the mouthpiece and/or reduction of the aerosol speed satisfactorily.

U.S. Pat. No. 4,592,348 B discloses a pressurized metered dose inhaler comprising the medication canister and a dispenser housing with an air passage running through it. The air channel of the dispensing aid is tapered from the air inlet opening towards the position of the dispensing port of the medication canister and then widens from there towards the aerosol outlet opening. Like this, a venturi throat is formed in the air passage. From the dispensing port, aerosol is dispensed into the center of the air stream in the direction of flow. U.S. Pat. No. 4,592,348 B discloses that the reduced air pressure within the venturi passage helps to atomise the liquid droplets of medication which enter the air passage through the dispensing port. No other function is described in the document. It does not provide any indication that its teachings may also be applied to nebulizers.

Figures 2, 3A:
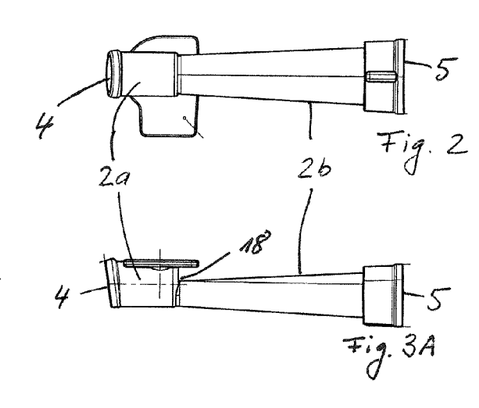
FIG. 2 shows a bottom view of the mixing channel 1 according to the invention.
FIG. 3A shows a side view of the mixing channel 1 according to the invention.

WO 2010/065616 A1 discloses a therapeutic treatment system comprising a delivery device for a cooled breathing gas mixture and an injection device positioned near a distal end of said delivery device. More specifically, the document discloses a respirator capable of forming and emitting a mist of fine ice particles for inhalation. The specific embodiment depicted in FIG. 3A shows a delivery device which is also shaped as a venturi element with a reduced cross-sectional area, so that the breathing gas mixture increases velocity and decreases pressure when flowing through said venturi element and over the fluid source. The lower pressure within the venturi element is described to draw fluid from the fluid source/the injection device into the venturi to mix it with air, thereby causing formation of droplets or a fine mist, which freeze to fine ice particles in the cooled gas mixture. Beyond this, WO 2010/065616 A1 does not disclose any further function. Moreover, it appears that a mixing channel is not necessary in the system of WO 2010/065616 A1. The injection device is positioned near a distal end of the therapeutic system (as can be seen in FIG. 3A), therefore the formed mist exits the device almost immediately, creating only a minor risk of droplet impaction on walls. In addition, the cooled breathing gas mixture provided by the respirator freezes said mist into fine ice particles, so that there is actually no risk of droplet coalescence as there is in an inhalation device comprising a nebulizer.

DE 10 2005 010 965 B3 and US 2009/0050137 A1 describe an inhalation device which employs a mixing channel. The inhalation device provided therein has a mixing channel that is especially adapted for supplying an aerosol to a patient's mouth in such a way that the droplets of liquid which are contained in the aerosol remain separated until they enter the mouth, throat, and lungs without being deposited on the wall of the mixing channel. The mixing channel comprises an air inlet and an aerosol outlet as well as an injection zone therebetween, for supplying a liquid drug through at least one nozzle orifice, which forms a part of the channel wall and is largely flush (height difference max 1 mm) with the channel wall's inner surface, at least at the side facing the air inlet. This avoids any projecting edges in the mixing channel, which would cause turbulences and increase the risk of droplets coalescence or deposition on the channel walls. The inhalation device uses one or more nozzle orifice(s) in order to inject jet(s) of droplets into the mixing channel at a certain angle $\alpha$ relative to the longitudinal axis of the channel.

The cross section of the channel is either constant or tapered from the air inlet to the injection zone. In a particular embodiment of US 2009/0050137 A1, the cross section of the mixing channel continuously decreases in successive longitudinal sections from a rectangular shape at the inlet to a rectangular shape with rounded corners across the injection zone, and then makes a transition from rectangular shapes with rounded corners and outwardly arched sides to a circular shape; see e.g. FIG. 13. The increased air velocity breaks up the initially continuous fluid jet(s) ejected from the nozzle orifice(s) into monodisperse droplets at a short distance from the nozzle and keeping them separated from one another and from the walls of the channel behind the so called mixing zone.

Figure 10:
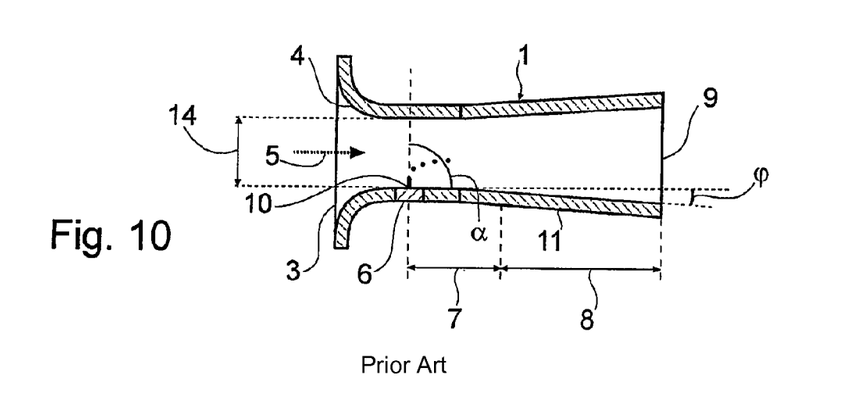
FIG. 10 shows a channel according to the prior art.

As described, the mixing channel of the device is formed such that its inner circumferential wall is smooth and continuous with respect to the intended direction of flow of the air stream. Thus, when being injected into the mixing channel, the droplets of agent are at first concentrated in the jet spilling out of the nozzle orifice. This is to say that the mixing process is then mainly performed by a diffusion process, i.e. the droplets diffuse into the air stream surrounding the jet. However, as the aerosol only remains a restricted time in the mixing channel, there is not enough time to achieve a spatially homogenous mixture of droplets and air. Indeed, since the jet is injected with a certain angle $\alpha$ into the air stream, e.g. $\alpha=90°$ (or any other angle between 10 and 170°), also small turbulences occur. However, they are relatively small due to the small size of the jet compared with the air stream; the jet rather bends in the air stream instead of being swirled, as depicted in FIG. 10 taken from US 2009/0050137 A1.

US 2009/0050137 A1 does not provide any teachings as to how their mixing channel (or, for instance, which particular shape out of the various ones suggested), could work with a continuously operating high output nebulizer such as a vibrating mesh nebulizer. In fact, it should be noted here that the nozzle plate described in DE 10 2005 010 965 B3 or US 2009/0050137 A1 with nozzle orifices arranged in a straight line perpendicular to the direction of the air stream is substantially different from perforated membranes of vibrating mesh nebulizers, which typically have ~300 up to ~9000 orifices, often arranged in circular or polygonal arrays.

The problem of insufficient mixing and/or deposition within the device is even more pronounced and important when using slow flow rates because these offer less dispersing and entraining qualities for the dense nascent aerosol emitted rapidly from the vibrating mesh. However, as described in various earlier publications by the inventors (e.g., WO 2010/089330 A1 or Griese et al.; Am. J. Resp. Critical Care Medicine, Vol. 169, 2004, pg. 822-828), it is exactly these slow inspiratory flow rates, such as below 20 L/min, preferably about 15 L/min, which are advantageous for drug delivery to the deeper lungs.

For the reasons discussed above, the mixture of the droplets into the air stream may remain incomplete when using a state-of-the-art mixing channel in combination with a continuously operating high output nebulizer such as a vibrating mesh nebulizer or an ultrasonic nebulizer, which results in an inhomogeneous distribution of droplets in the aerosol. Thus, there is a need for a mixing channel that allows for an improved mixing process resulting in a homogenous distribution of droplets in the aerosol.

Therefore, the object of the present invention is to provide a mixing channel that allows for an improved mixing process resulting in a homogenous distribution of droplets in the aerosol. Another object of the invention is to provide an inhalation device comprising such a mixing channel. A further object is to reduce the loss of aerosol droplets in an inhalation device due to coalescence and/or deposition within the device. A yet further object is to provide a mixing channel of comparatively small outer dimension, which render it suitable for an optional application in small, mobile (i.e., portable), handheld inhalation devices. This object is achieved by a mixing channel for an inhalation device and an inhalation device with the features according to the claims attached hereto.

The idea of the mixing channel of the present invention is to provide a step in the mixing channel's inner wall, or any other means which abruptly decrease the effective cross sectional area of the mixing channel. In contrast to the prior art, wherein—as described above—the mixing channel comprises a smooth and continuous inner circumferential surface, thereby avoiding the occurrence of swirling processes, the mixing channel according to the present invention comprises a step on its inner circumferential surface, i.e. a discontinuity in the direction of flow. As used herein, a step is a substantial or abrupt change in the cross sectional area at a longitudinal locus or within a short longitudinal section of the mixing channel. According to the invention, the cross sectional area decreases more or less abruptly within or at the downstream end of the injection zone. For example, the step may be formed so as to obstruct about 50% of the cross section of the mixing channel. The injection zone, as used herein, is that part of the mixing channel where the injection of the nascent aerosol occurs and/or where the aerosol emitted from the nebulizer is initially mixed with air. The injection zone, as well as other features of the invention, will be defined in further detail, also in combination with the figures. Herein, a step is understood as an offset or change in the level of the inner surface of the mixing channel, the step being formed by three successive surface portions. The angle between two neighboring surface portions is in a range from 80°-100°, preferably 85°-95°, more preferably essentially 90°, and most preferably 90°.

Figure 1A:
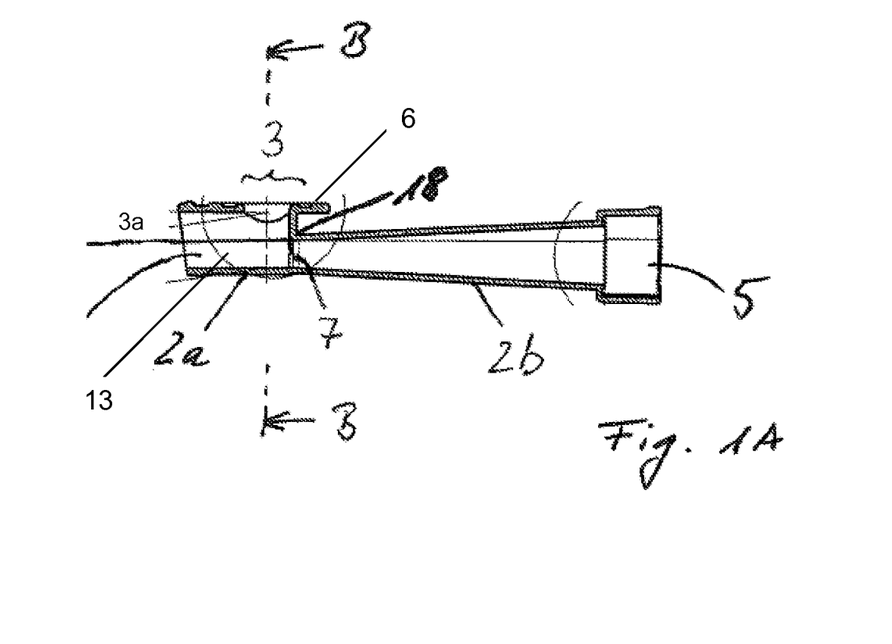
FIG. 1A shows a vertical section through the longitudinal center axis of an embodiment of the mixing channel 1 according to the invention.

The process of equally distributing the droplets into the air stream is further supported by the fact that the mixing channel is restricted to a smaller effective cross section (compared to the inlet opening) through the step, and immediately behind the step, and only gradually increases again towards the outlet opening. That is to say that the reduced cross sectional area is owed to an actual step rather than just a baffle-type wall protruding from an inner wall; as can be seen in FIG. 1A. Here, the term "effective cross section" shall denote that part of the cross section that is actually open to the air stream, i.e. that part of the cross section that is confined by the inner circumferential wall of the mixing channel, independently of the mixing channel's outer circumferential wall that may not reflect the step. Further, the wording "behind the step" as well as all similar terms designating a position, orientation or direction shall be related here and in the following to the intended direction of flow of the air stream in the mixing channel, i.e., from inlet opening to outlet opening.

Due to the restricted cross section, the flow profile and the flow rate, more precisely the velocity, of the air flow changes at the position of the step in that the air and the aerosol undergo an acceleration there. According to the invention, as will be described later in detail, the nebulizer is placed directly adjacent to, i.e. in front of, the step in the mixing channel or forms the step itself, as can e.g. be seen in FIG. 11B. Typically, only a part of the nebulizer is actually inserted and protruding into the mixing channel, not the whole nebulizer. In the specific embodiment depicted in FIGS. 11A and B, this inserted part comprises the downstream end of a vibrating mesh nebulizer which has affixed the vibrating mesh at its bottom from where the nascent aerosol is emitted. Consequently, the jet of droplets is injected at or directly behind the step into the mixing channel, i.e. at a position with high air velocity. As the air is accelerated here compared with upstream or in front of the step, the density of the nascent aerosol in the air stream is kept small (in comparison to the case that the droplets were injected into an air stream with a lower velocity—like, e.g., before the step) because the droplets are rapidly entrained and diluted in the fast air stream. A decreased density is of the advantage that the average distance between the droplets is increased and so an unwanted coalescing of the droplets— that would lead to larger average diameters of the droplets— can be largely avoided or reduced.

Furthermore, as the shape of the mixing channel behind the step is preferably a truncated cone that widens towards its downstream end, a deposition of the droplets on the inner wall of the mixing channel can be avoided or reduced. These depositions can be further reduced by a suitable anti-static coating material.

Moreover, the accelerated air stream behind the step becomes decelerated again due to the trumpet-like shape of the truncated cone. This way, at the outlet of the mixing channel, the flow is reduced so that it attains a value suitable for the inflow into the patient's mouth without impaction and for the transport into the deeper lung areas. Thus, the mixing channel behind the step is shaped such as to act as a diffuser.

Unexpectedly, it was found by the inventors that the mixing channel of the invention achieves a sufficiently large acceleration of the air flowing inside the channel at a moderate flow rate (of e.g. 15 l/min) to ensure that an aerosol, even when emitted by a nebulizer having a high output rate (such as about 0.5 ml/min or more, or about 0.8 or more, or even about 1 ml/min or more) from the top into the mixing zone at an angle of about 90° relative to the longitudinal center axis of the mixing channel, is rapidly mixed with the air and diluted without substantial impaction on the wall of the mixing channel and without substantial coalescence. It was also surprising to find that the mixing channel as described herein could be miniaturised and still be effective to achieve these results. It is noted that the conditions mentioned above, i.e. the incorporation of a highly efficient nebulizer in an inhalation device adapted for a slow inspiratory flow rate are particularly challenging with respect to the propensity of the nascent aerosol to coalesce and become deposited within the device.

Depending on the flow rate within the mixing channel, it was observed that the abrupt decrease of the effective cross sectional area at the step may lead to a rapid deflection and acceleration of the flowing air even without substantially interfering with a laminar flow. This was confirmed by computational flow simulations.

One aspect of the invention relates to a mixing channel for an inhalation device, comprising an inlet opening, an outlet opening, and an injection zone located between the inlet opening and the outlet opening. The injection zone has a longitudinal center axis and comprises (a) a built-in nebulizer, or (b) a detachable nebulizer, or (c) a member adapted to receive a detachable nebulizer. Furthermore, the effective cross sectional area of the mixing channel in a plane perpendicular to the longitudinal center axis is smaller in the injection zone than upstream of the injection zone. More specifically, the effective cross sectional area of the mixing channel in a plane perpendicular to the longitudinal center axis decreases abruptly in the direction of air flow within or at the downstream end of the injection zone such that said cross sectional area is smaller in the injection zone than upstream of the injection zone. The abrupt decrease in cross sectional area preferably forms a step in the mixing channel.

Optionally, the shape of the cross sectional area is circular or elliptical, alternatively rectangular, at the upstream end of the injection zone and becomes semi-circular or semi-elliptical at the downstream end of the injection zone.

As defined herein, the shape of cross sectional areas with an aspect ratio (i.e., the ratio between the largest diameter and the smallest diameter orthogonal to it) of not more than ~1.3:1 are considered circular or approximately circular, whereas those with aspect ratios larger than ~1.3:1 will be considered elliptical. In analogy, the terms "approximately semi-circular" or "approximately semi-elliptical" refers to shapes which resemble circular or elliptic ones cut in halves; optionally with rounded edges and/or the circumferential lines slightly arching outwards.

Depending on the precise shape of the approximately semi-circular or semi-elliptical cross section, the size of the cross sectional area is decreased abruptly at the downstream side of the injection zone to about half the area, or slightly less, compared to the area on the upstream side of the injection zone. One example of an approximately semi-circular cross section according to the invention is depicted in FIG. 11C.

Throughout the following, the term "direction of flow" shall be understood as the direction from the inlet opening to the outlet opening of the mixing channel.

One aspect of the invention relates to a mixing channel comprising a first channel portion and a second channel portion downstream of the first channel portion. The first channel portion comprises the inlet opening and the injection zone. The built-in nebulizer, detachable nebulizer or member adapted to receive a detachable nebulizer is in, or extends from, a lateral position relative to the longitudinal center axis of the injection zone. Preferably, the built-in nebulizer, or the detachable nebulizer, or the member adapted to receive a detachable nebulizer are arranged or located on a longitudinal side portion or side wall of the mixing channel. Thus, the built-in nebulizer, or the detachable nebulizer may be arranged in a direction transversal to the longitudinal direction or axis of the mixing channel.

One aspect of the invention relates to a mixing channel, wherein the built-in nebulizer protrudes into the mixing channel. Alternatively, the detachable nebulizer protrudes into the mixing channel. Such "protruding" or extension is preferably not beyond the longitudinal center axis of the mixing channel.

A further aspect of the invention relates to a mixing channel, wherein the built-in nebulizer or the detachable nebulizer is arranged in the injection zone such that the effective cross sectional area of the mixing channel in a plane perpendicular to the longitudinal center axis is smaller in the injection zone, or at the downstream end of the injection zone, than upstream of the injection zone. More specifically, the built-in nebulizer or the detachable nebulizer extends from a lateral position relative to the longitudinal center axis (A) of the injection zone (3) and protrudes into the injection zone (3) such that the size of the effective cross sectional area of the mixing channel in a plane perpendicular to the longitudinal center axis (A) decreases abruptly in the direction of air flow within or at the downstream end of the injection zone (3).

A further aspect of the invention relates to a mixing channel, wherein upon the detachable nebulizer being received in said member, the effective cross sectional area of the mixing channel in a plane perpendicular to the longitudinal center axis is smaller in the injection zone than upstream of the injection zone. More specifically, this aspect of the invention relates to a mixing channel, wherein upon the detachable nebulizer being received in said member, the size of the effective cross sectional area of the mixing channel in a plane perpendicular to the longitudinal center axis is decreased abruptly within or at the downstream end of the injection zone (3).

In other words, while the step may be formed by the size and shape of the walls of the mixing channel and its openings as such, the inserted nebulizer which protrudes into the mixing channel may also be understood as forming a step.

As already described, the mixing channel comprises a first channel portion and a second channel portion downstream of the first channel portion. Preferably, the inner surface of the wall of the mixing channel forms a continuous or step-free transition between the downstream end of the first channel portion and the upstream end of the second channel portion on the side opposite to the built-in nebulizer, detachable nebulizer or member adapted to receive a detachable nebulizer. In other words, the step is primarily formed on that side of the mixing channel where the nebulizer or member adapted to receive the nebulizer is located, whereas the opposite side is shaped in such a way that it does not, or not significantly, contribute to the step.

The first channel portion preferably comprises the inlet opening forming an air inlet, and a member adapted to receive a detachable nebulizer, which may be realized by a through-hole. The first channel portion may be shaped as a preferably circular, but optionally also elliptic or rectangular, cylinder with a longitudinal center axis A. This cylinder is preferably confined at its upstream end by the inlet opening, which can be considered as a cut through the cylinder along a cross sectional plane, which is not necessarily orthogonal to the longitudinal center axis A.

The inlet opening may thus be shaped as a preferably circular, but optionally also elliptic. Alternatively, the inlet opening is rectangular, for example with right-angled corners or with rounded corners.

The through-hole may be arranged at the very downstream end of the first channel portion on one side of the circumferential wall of the cylinder. At its downstream end, the first channel portion may be partially closed by a wall that is arranged on a cross sectional plane orthogonal to the longitudinal center axis A; i.e. the step. Thereby, the wall may be arranged so as to cover approximately 50% of the cross sectional size at downstream end of the first channel portion on the side of the through-hole. The remaining opening of the downstream end of the first channel portion may be formed as an approximate semi-circle. Alternatively, the remaining opening of the downstream end of the first channel portion may be formed approximately semi-elliptical, such as e.g. when the first segment of the mixing channel is shaped as an elliptical cylinder.

In this embodiment, the downstream opening, or end, of the first channel portion is at the same time the upstream opening, or end, of the second channel portion. That is, it forms a transition opening between the first and the second channel portion. Thus, the transition opening between the first channel portion and the second channel portion forms a virtual section or plane distinguishing the first channel portion from the second channel portion. Because of said wall partially closing the downstream end of the first channel portion, a step is formed at the site of the transition between both channel portions.

The first channel portion may also be understood as a mixing chamber. According to an aspect of the invention, a mixing chamber for an inhalation device is provided which has a substantially cylindrical or cylindroidal wall and a substantially first, for example horizontal, orientation. The mixing chamber comprises an inlet opening at its upstream end, a mixing chamber outlet opening (which is identical with the transition opening mentioned above) at its downstream end, and an injection zone for aerosol. Moreover, it includes a built-in or detachable nebulizer extending from the top of the mixing chamber such as to protrude into the injection zone and to emit aerosol at or near the longitudinal center axis of the injection zone at an angle of 90° or an angle from 45° to 135° with respect to the longitudinal center axis A of the injection zone. The mixing chamber outlet opening may have a substantially second, for example vertical, orientation and be positioned between the longitudinal center axis and the wall of the mixing chamber opposite of the position from which the nebulizer extends into the mixing chamber.

As mentioned, the inlet opening may optionally be circular or elliptic. Optionally, the diameter or, in the case of an elliptic opening, the average diameter may be in the range from about 5 to 15 mm, in particular from about 7 to about 12 mm, such as from about 8 to about 10 mm.

The outlet opening of the mixing channel may be connectable with a mouthpiece for inhalation by a user. The mouthpiece may comprise an inner part and an outer part. The inner part of the mouthpiece is connected to the downstream end of the second channel portion, for example by means of an air tight pressfit. Thereby, the inner part of the mouthpiece acts as or forms an extension of the second channel portion. Furthermore, the connection between the inner part of the mouthpiece and the second channel portion may be formed as a continuous or step-free transition. This way, the profile of an air stream propagating through the mixing channel is not disturbed in the area of this connection. When being connected to the mixing channel, the outer part of the mouthpiece may cover approximately two thirds of the second channel portion of the mixing channel on the downstream side. Thus, part of the outer part of the mouthpiece surrounds the inner part of the mouthpiece in a concentric manner.

Alternatively, the second channel portion and the mouthpiece may be shaped as one single part.

One aspect of the invention relates to a mixing channel, wherein the longitudinal center axis of the second channel portion and the longitudinal center axis of the injection zone form an angle of preferably 180°; i.e. they are parallel to each other.

One aspect of the invention relates to a mixing channel, wherein the longitudinal center axis of the second channel portion and the longitudinal center axis of the injection zone form an angle of preferably not less than 172°. In other words, if the two axes are not parallel, they should form an obtuse angle of not less than 172°, i.e. in the range of 172° to 180°.

As described earlier, the built-in nebulizer or the detachable nebulizer protrudes into the injection zone of the mixing channel. One aspect of the invention relates to a mixing channel, wherein the built-in nebulizer or detachable nebulizer is positioned such as to emit the aerosol at the longitudinal center axis of the injection zone, or near and towards the longitudinal center axis of the injection zone. As used herein, the expression "near the longitudinal center axis" should be understood to describe that the downstream end of the nebulizer is substantially closer to the longitudinal center axis than to a lateral wall of the mixing channel.

One aspect of the invention relates to a mixing channel, wherein the nebulizer (be it the built-in nebulizer or the inserted detachable nebulizer) is flush with a part of the inner surface of the wall of the mixing channel downstream of the injection zone. In other words, the end of the downstream part of the nebulizer is flush with the step, which is e.g. the case if both the downstream end of the nebulizer and the highest point of the transition opening (or of the mixing chamber outlet opening) are at or near the longitudinal center axis of the mixing channel.

One aspect of the invention relates to a mixing channel, wherein the shape of the cross sectional area of the mixing channel downstream of the injection zone is inconstant. One aspect of the invention relates to a mixing channel, wherein the size of the cross sectional area of the mixing channel downstream of the injection zone is inconstant. One aspect of the invention relates to a mixing channel, wherein the shape and the size of the cross sectional area of the mixing channel downstream of the injection zone is inconstant.

More specifically, one aspect of the invention relates to a mixing channel, wherein the cross sectional area of the mixing channel downstream of the injection zone increases in size along the direction of flow. Preferably, the cross sectional area increases continuously. In this respect, the term continuously is to be understood such that the increases in cross sectional area are not stepwise but steadily, so as to leave the inner walls of the second segment of the mixing channel (i.e. downstream of the injection zone) smooth and free of edges, in order to avoid or reduce turbulences and/or flow stalls here which could cause deposition of aerosol droplets within the second segment.

The second channel portion may essentially be formed as a truncated cone or tapered elliptical cylinder. Due to the step mentioned above, the second channel portion may not be symmetrical or coaxial with respect to the longitudinal center axis A of the first channel portion.

The widening of the channel in the second segment serves to decrease the velocity of the aerosol so that the decelerated aerosol droplets are not deposited in the throat of the user, but reach the lungs.

The second channel portion is preferably shaped as follows: Taking a sequential series of cross sections of the second channel portion from the upstream to the downstream end (each of the cross sections being orthogonal to the longitudinal center axis A of the first channel portion), the first cross section has an approximately semi-circular or semi-elliptical shape corresponding to the upstream opening, or transition opening, of the second channel portion. Then, the shape of each of the subsequent cross sections extends over the shape of the respective previous cross section. The cross section having the largest size out of that series corresponds to the downstream opening of the second channel portion. The downstream opening of the second channel portion forms at the same time the outlet opening of the mixing channel.

One aspect of the invention relates to a mixing channel, wherein the opening angle, which is roughly twice the angle α between the center axis of the second channel portion and any tangential plane (i.e. that line of the tangential plane which is also part of a longitudinal section) on the inner surface of the second channel portion, is not more than about 8°.

Due to this limitation, stalls and turbulences potentially causing aerosol deposition in the second segment can be largely avoided.

One aspect of the invention relates to a mixing channel, wherein the opening angle as described herein is not more than about 6°. For example, the opening angle may be about 5°, about 5.5°, or about 6°.

One such alternative of the invention relates to a mixing channel, wherein the opening angle is constant or approximately constant (i.e., in the form of a truncated cone).

With regard to the opening angle, and/or the angle α which is roughly half of the opening angle, it should be noted that these angles may differ slightly depending on the particular longitudinal section under consideration. Since the shape of the transition opening and the air outlet may differ somewhat, the respective opening angle of the second segment along a horizontal longitudinal section may also slightly differ from that of a vertical longitudinal section. In this case, the opening angle should be understood as the mean opening angle along any such longitudinal section. For example, an opening angle of not more than about 8° (i.e., a not more than about 4°) or alternatively not more than about 6° (i.e., a not more than about 3°) refers to the mean value of the respective angles for different longitudinal sections.

Moreover, in case the downstream end of the second segment at the outlet opening is rounded such as to avoid sharp edges, this rounded downstream end should not be taken into consideration when determining the mean angles.

The term "constant", when referring to the opening angle and/or angle α, is to be understood as meaning constant along a longitudinal section on an inner surface of the second channel portion from the transition opening nearly to the outlet opening (not taking a rounded downstream end into account). In other words, the line where the longitudinal section intersects the inner surface of the second segment is a straight line, at least for most of its length, such as over 80% of its length or more, or even over 90% of its length or more. For example, the opening angle could be about 5° at the upstream opening, or transition opening, of the second mixing channel segment as well as about 5° further downstream.

Another alternative of the invention relates to a mixing channel, wherein the angle between the center axis of the second channel portion and a tangential plane on the inner surface of the second channel portion is increasing along the direction of flow. For example, the (mean) opening angle could be about 5° at the upstream opening, or transition opening, of second segment and increase to about 6° towards the outlet opening of second mixing channel segment.

One aspect of the invention relates to a mixing channel, wherein the built-in nebulizer or detachable nebulizer is positioned such as to emit the aerosol into the mixing channel at an angle of 90° or at an angle within a range from 45° to 135°, preferably 60° to 120°, more preferably 85° to 95° with respect to the longitudinal center axis A of the injection zone. This is of particular importance for vibrating mesh nebulizers, where the liquid is supposed to flow freely and gravity-driven from a reservoir to a horizontally arranged vibrating mesh, and more pronounced tilting of the nebulizer could result in spillage, deceleration of aerosol output, and/or incomplete aerosolization of the liquid formulation.

One aspect of the invention relates to a mixing channel, wherein the inlet opening of the mixing channel forms the inlet opening of the inhalation device.

One aspect of the invention relates to a mixing channel, wherein the inlet opening of the mixing channel is connectable with an inlet channel of the inhalation device.

One aspect of the invention relates to a mixing channel, wherein the reduction of the cross section area of the mixing channel in the area of the injection zone is configured such as to cause a change in the flow profile of a medium when the medium is streaming through the mixing channel.

One aspect of the invention relates to a mixing channel, comprising a filter positioned upstream of the injection zone, preferably near the inlet opening. The filter is preferably a hydrophobic filter with a low flow resistance. The filter may be made from polyester. "Low flow resistance" preferably means that it effects a pressure drop of not more than 5 mbar at a flow of 15 L/min. The use of such a filter may be valuable for retaining air borne particles which could introduce uncontrollable turbulences and interfere with the laminar flow of the air stream within the mixing channel.

One aspect of the invention relates to a mixing channel, wherein the inner surface of the wall of the mixing channel is at least partially coated with a layer of a biocompatible material, wherein said biocompatible material is preferably antistatic and/or made from poly(p-xylylene).

In a further aspect, the built-in nebulizer or detachable nebulizer is an ultrasonic nebulizer or a vibrating mesh nebulizer. As used herein, a nebulizer means an aerosol generator, or atomiser, capable of converting a non-pressurised liquid into an inhalable aerosol in a continuous manner. In particular, the built-in or detachable nebulizer is a vibrating mesh nebulizer, i.e. a nebulizer with a mesh, or perforated membrane, through which the liquid which is to be nebulised is extruded by means of vibration. Typically, the perforated membrane is vibrated by a piezo element (thus the expression, vibrating mesh nebulizer); however, it may also be possible to vibrate the liquid rather than the membrane and thereby generate the aerosol.

It is particularly useful to practise the invention by using a nebulizer with a high output rate. In this context, the output rate of the nebulizer means the amount of liquid which is converted into an aerosol per time unit. Optionally, a nebulizer with an output rate of at least about 0.5 ml/min is selected. The output rate may also be at least about 0.8 ml/min, or at least about 1.0 ml/min, respectively.

One aspect of the invention relates to a mixing channel, wherein the built-in nebulizer or detachable nebulizer comprises a main member, preferably a turned part, a ring member made of piezoelectric material, and a perforated membrane, wherein the main member comprises a tubular portion comprising an outer area exhibiting a ring-shaped widening onto which the ring member is attached such that the main member extends through the ring member, and the perforated membrane being connected into or onto the front part of the main member; and the main member being connectable with a liquid drug reservoir.

One aspect of the invention relates to a mixing channel, wherein the built-in nebulizer or detachable nebulizer is connected to the mixing channel in an air-tight manner, and preferably by means of a sealing lip. The sealing lip is preferably produced by two component molding.

A further aspect of the invention relates to an inhalation device comprising one embodiment of the mixing channel according to the invention. The inhalation device may comprise a case or housing and a mouthpiece. The mouthpiece may be connected with the second channel portion of the mixing channel, as described above, or it may itself represent the second channel portion.

One aspect of the invention relates to an inhalation device, wherein the mixing channel according to the invention is connected with the inhalation device in an air-tight manner, and preferably by means of a sealing lip, wherein the sealing lip is preferably produced by two component molding.

The inhalation device may comprise a main body which may be covered by or received in a base piece of the housing. The main body may comprise a chamfer or recess into which the mixing channel may be detachably placed. Thereby, the mixing channel is placed so into the main body that the through-hole is located on the side opposite to the main body or opposite to the base piece of the housing. Onto the through-hole may be placed a reservoir member holding a drug reservoir, configured to receive a liquid drug formulation. Furthermore, a nebulizer may be either comprised within the reservoir member or attached thereto. An exemplary inhalation device suitable for incorporating a mixing channel according to the invention is described, for instance, in the co-pending European patent application number 12 19 0139.1 or the international application PCT/EP2012/076963.

In a further aspect, the inhalation device is adapted for, or configured to, allowing the user to inhale air and/or aerosol through the mouthpiece at an inspiratory flow rate of not more than about 20 l/min, such as from about 10 to 20 l/min, or from about 12 to 18 l/min, such as about 15 l/min. Optionally, the inhalation device may comprise a feature which restricts the air flow, e.g. by means of a responsive flow restrictor, to a particular maximum flow rate, of e.g. 20 l/min or 18 l/min. Alternatively, or in addition, the inhalation device may provide the use with visible, audible or tactile feedback or guidance such as to enable the user to inhale at the desired inspiratory flow rate.

Other aspects, features, and advantages will be apparent from the summary above, as well as from the description that follows, including the figures and the claims.

LIST OF FIGURES

FIG. 10 refers to prior art.

FIG. 1A shows a vertical section through the longitudinal center axis of an embodiment of the mixing channel 1 according to the invention. The mixing channel 1 comprises a first channel portion 2a and a second channel portion 2b. The first channel portion 2a comprises an inlet opening 4 forming an air inlet, and a member adopted to receive a detachable nebulizer, which is realized here by a through-hole 3a. Thereby, the first channel portion 2a is shaped as a cylinder with a longitudinal center axis A. This cylinder is confined at its upstream end by the inlet opening 4, which can be considered as a virtual cut through the cylinder along a cross sectional plane, which is not necessarily orthogonal to the longitudinal center axis A. The through-hole 3a is arranged at the very downstream end of the first channel portion 2a on one side of the circumferential wall of the cylinder. At its downstream end, the first channel portion 2a is partially closed by a wall that is arranged on a cross sectional plane orthogonal to the longitudinal center axis A. Thereby, the wall is arranged so as to cover approximately 50% of the downstream end of the first channel portion 2a on the side of the through-hole 3a. The remaining opening of the downstream end of the first channel portion 2a is formed as an approximate semi-circle, as shown in detail in FIGS. 3B and 3C as well as FIG. 11C (therein, cf. reference numeral 7 labelling the transition opening explained below).

The downstream opening of the first channel portion 2a is at the same time the upstream opening of the second channel portion 2b; in other words, it forms a transition opening 7 between the first and the second channel portion. Thus, the transition opening 7 between the first channel portion 2a and the second channel portion 2b forms a virtual section or plane distinguishing the first channel portion 2a from the second channel portion 2b. Because of said wall partially closing the downstream end of the first channel portion 2a, a step 18 is formed at the site of the transition between channel portions 2a and 2b. The second channel portion 2b is essentially formed as a truncated cone or tapered elliptical cylinder. Due to the step 18, the second channel portion 2b is not symmetrical or coaxial with respect to the longitudinal center axis A of the first channel portion 2a.

The second channel portion 2b is formed as follows (cf. FIGS. 1 and 3B together): Taking a sequential series of cross sections of the second channel portion 2b from the upstream to the downstream end (each of the cross sections being orthogonal to the longitudinal center axis A of the first channel portion 2a), the first cross section has a semi-circular shape corresponding to the upstream opening of the second channel portion 2b. Then, the shape of each of the subsequent cross sections extends over the shape of the respective previous cross section. The cross section having the largest size out of that series corresponds to the downstream opening of the second channel portion 2b. The downstream opening of the second channel portion 2b forms at the same time the outlet opening 5 of the mixing channel 1. The outlet opening 5 may be connectable with a mouthpiece for inhalation by a user.

Figure 1B:
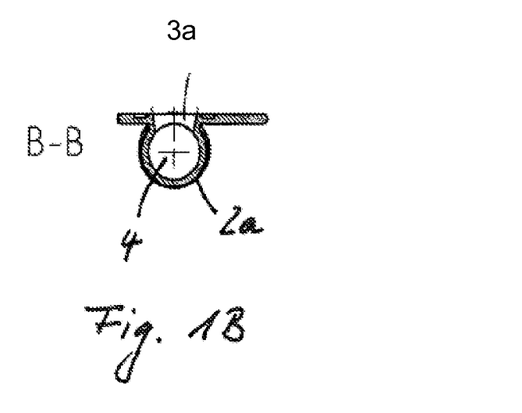
FIG. 1B shows a cross section of the first channel portion 2a of mixing channel 1 according to B-B in FIG. 1.

FIG. 1B shows a cross section of the first channel portion 2a mixing channel 1 along the line B-B depicted in FIG. 1A. The circumferential wall of the first channel portion 2a is essentially formed as a, preferably circular, cylinder. On one side of the cylinder, a through-hole 3a is arranged, which acts as a member 6 adapted to receive a detachable nebulizer.

Figure 4:
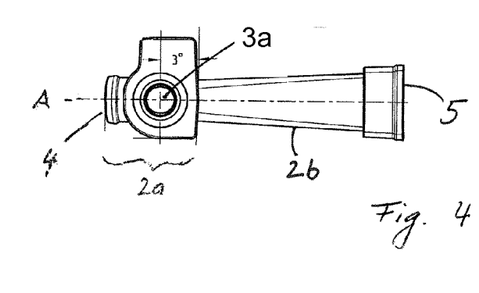
FIG. 4 shows a top view of the mixing channel 1 according to the invention.

FIGS. 2, 3A, and 4 show, respectively, a bottom view, a side view, and a top view of an embodiment of the mixing channel 1 according to the invention. The first channel portion 2a comprises at its upstream end the inlet or rear opening 4. At or near or adjacent to the downstream end of the first channel portion 2a, a through-hole 3a is arranged. Directly behind (with respect to the direction from the upstream to the downstream end) the through-hole 3a, a step 18 is formed by a wall arranged perpendicular to the longitudinal center axis A of the first channel portion 2a, the wall partially closing the downstream end of the first channel portion 2a. Downstream of the first channel portion 2a, the mixing channel 1 comprises the second channel portion 2b formed as a tapered elliptical cylinder with the outlet opening 5 at its downstream end.

Figure 3B:
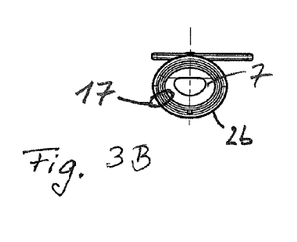
FIG. 3B shows the mixing channel 1 seen from side of the outlet opening 5.

FIG. 3B shows an embodiment of the mixing channel 1 as seen from the side of the outlet or front opening 5, i.e. a front view, wherein the second channel portion 2b formed as a tapered elliptical cylinder. A number of concentric ellipsoidal contour lines 17 visualize the tapered shape of the second channel portion 2b. The approximately semi-circular contour line 7 depicts the transition opening between the first channel portion 2a and the second channel portion 2b. In this context, please be also referred to the description of FIG. 1 given above.

Figure 3C:
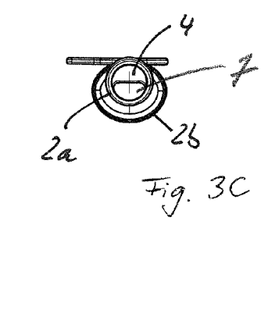
FIG. 3C shows the mixing channel 1 from the side of the inlet opening 4.

FIG. 3C shows the same mixing channel 1 as in FIG. 3B now from the side of the inlet opening 4, i.e. a rear view. Seen from this side, the first channel portion 2a appears as a circle. Inside the inlet opening 4, the transition opening 7 between the first channel portion 2a and the second channel portion 2b is visible as a semi-circular shape. The contour of the second channel portion 2b is visible behind the inlet opening 4 as an ellipsoidal profile.

Figure 5:
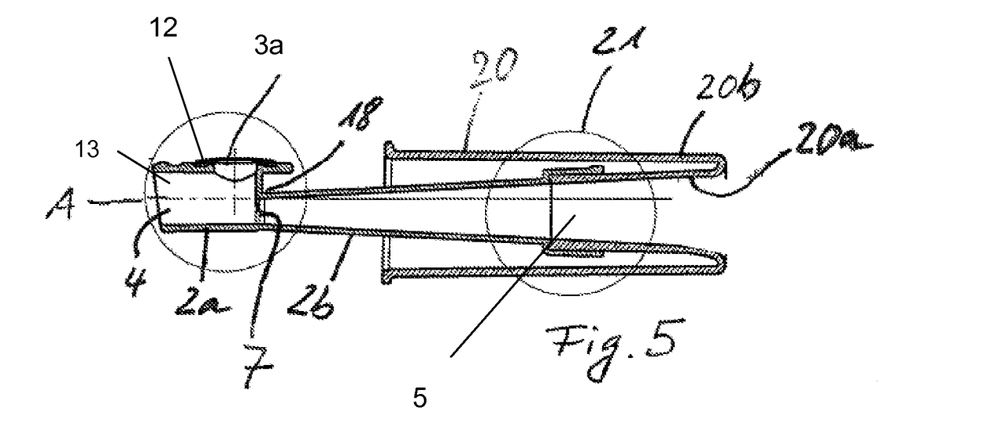
FIG. 5 shows a vertical section through the longitudinal center axis of another embodiment of the mixing channel 1.

FIG. 5 shows the view of a vertical section through the longitudinal center axis of another embodiment of the mixing channel 1 according to the invention similar to FIG. 1a, which is connected to a mouthpiece 20. The mouthpiece 20 comprises an inner part 20a and an outer part 20b. The inner part 20a of the mouthpiece 20 is connected to the outlet opening 5 at the downstream end of the second channel portion 2b, for example by means of an air tight press-fit 21. Thereby, the inner part 20a of the mouthpiece 20 acts as or forms an extension of the second channel portion 2b. Furthermore, the connection between the inner part 20a of the mouthpiece 20 and the second channel portion 2b is formed as a continuous or step-free transition. This way, the profile of an air stream propagating through the mixing channel 1 is not disturbed in the area of this connection. When being connected to the mixing channel 1, the outer part 20b of the mouthpiece 20 may cover, for example, approximately two thirds of the second channel portion 2b of the mixing channel 1 on the downstream side.

Figure 6:
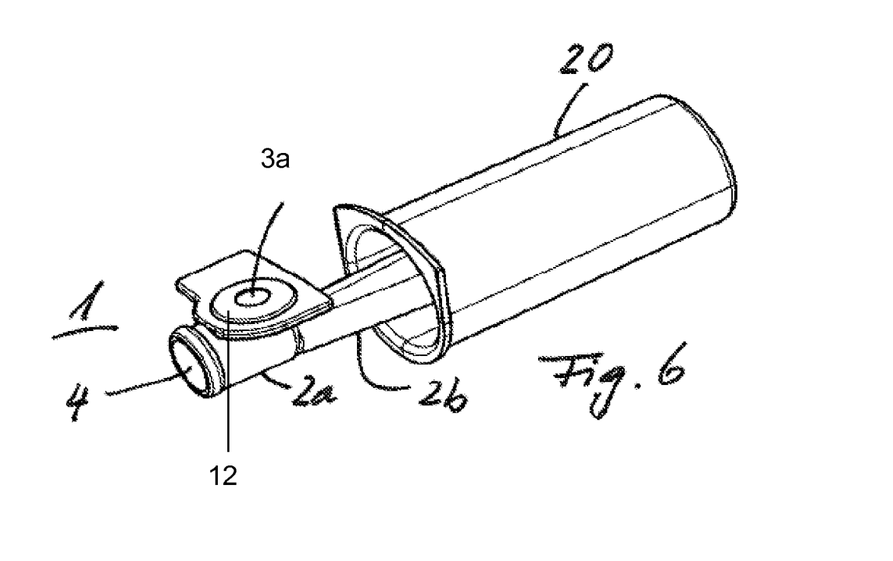
FIG. 6 shows a perspective view of the mixing channel 1 connected to the mouthpiece 20.

FIG. 6 shows a perspective view of the mixing channel 1 connected to the mouthpiece 20. The connection site is located inside the outer circumferential wall of the mouthpiece 20 and therefore not visible. The upstream end of the second channel portion 2b extends out of the mouthpiece 20 and is therefore visible. FIG. 6 gives also a three dimensional view of the first channel portion 2a comprising the inlet opening 4 and the through-hole 3a and connected to the upstream end of second channel portion 2b. Through-hole 3a is surrounded by a sealing lip 12.

Figure 7:
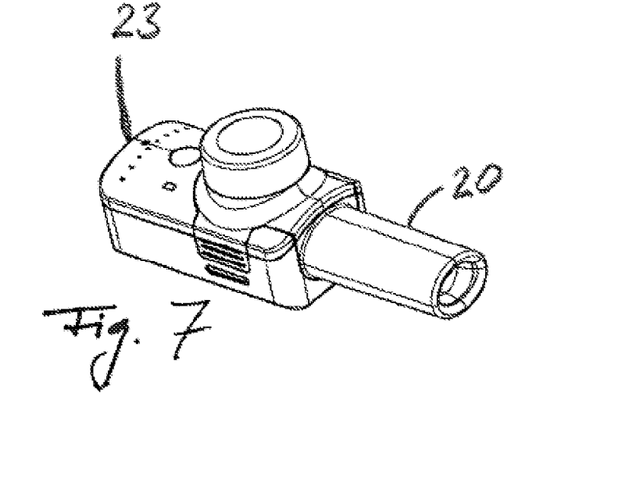
FIG. 7 shows an inhalation device comprising the mixing channel 1.

FIG. 7 shows an inhalation device comprising the mixing channel 1 according to the invention. The inhalation device comprises a case or housing 23 and the mouthpiece 20. However, the mixing channel 1 itself is not visible from this perspective, since its upstream part is located inside the inhalation device, and the downstream part is covered by the mouthpiece 20.

Figure 8:
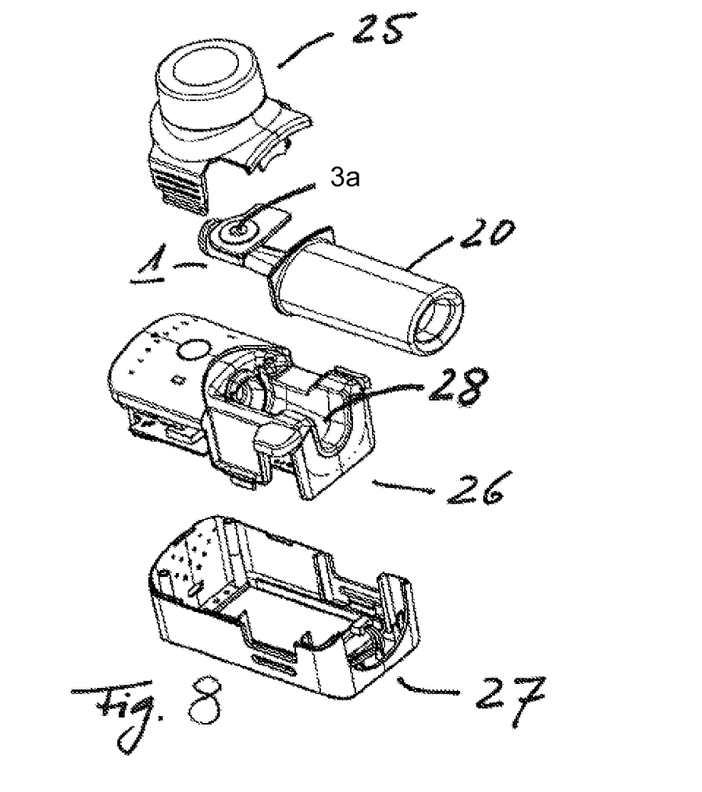
FIG. 8 is an exploded view of the inhalation device shown in FIG. 7.

FIG. 8 is an exploded view of the inhalation device shown in FIG. 7. A main body 26 is covered or received in a base piece 27 of a housing. The main body 26 comprises a chamfer 28, into which the mixing channel 1 (preferably) connected to a mouthpiece 20 is placed. Thereby, the mixing channel 1 is placed so into the chamfer 28 that the through-hole 3a is located on the side opposite to the main body 26 or opposite to the base piece 27. Onto the through-hole 3a is placed a reservoir member 25 including a reservoir for a liquid drug formulation (not shown). Furthermore, a nebulizer (not shown in FIG. 8, cf. FIG. 9) may be comprised within the reservoir member 25, optionally in direct contact with the drug reservoir.

Figure 9:
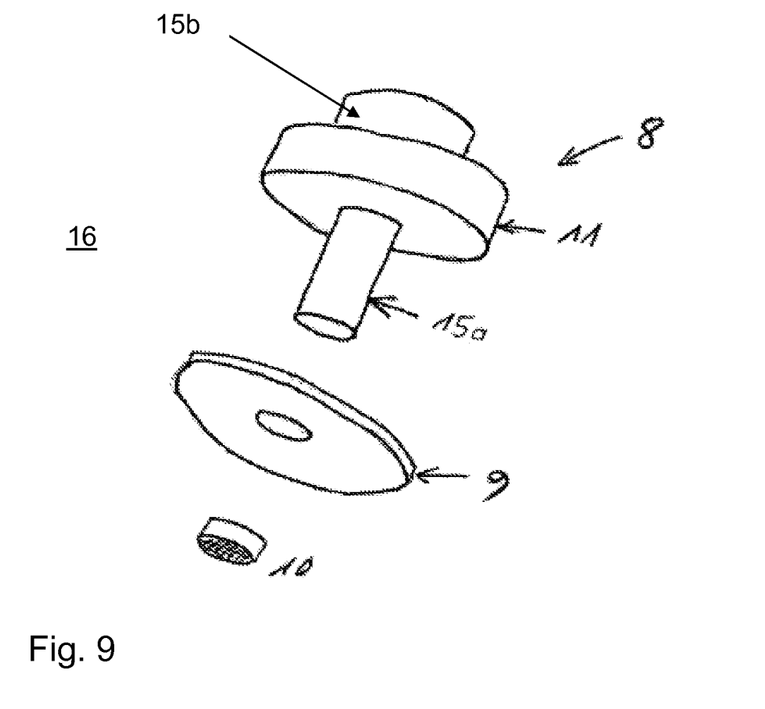
FIG. 9 shows an exploded view of a nebulizer configured to be inserted into the through-hole 3a of the mixing channel 1.

FIG. 9 shows an exploded view of a nebulizer 16 configured to be inserted into the through-hole 3a of the mixing channel 1. The depicted nebulizer 16 may be a built-in nebulizer or a detachable nebulizer. The nebulizer comprises a main member 8 formed as a turned part. The main member 8 comprises a tubular portion comprising an outer area exhibiting a ring-shaped widening 11. A ring member 9 made of piezoelectric material is attached to the ring-shaped widening 11 such that the main member 8 extends through the ring member 9. Further, a perforated membrane 10 is connected into or onto the downstream part, or front part, 15a of the main member 8. The main member 8 is connectable with a drug reservoir (not shown) for a liquid drug at its upstream end 15b. Typically, only the downstream part 15a of the nebulizer 16 is inserted in the through-hole 3a, not the whole nebulizer 16.

FIG. 10 shows a channel according to the prior art.

Figure 11A:
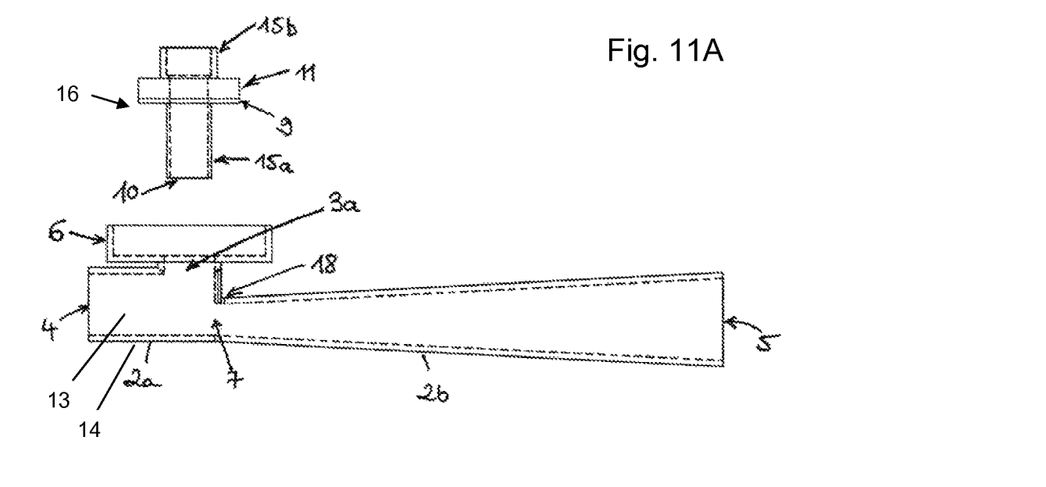
FIG. 11A shows a vertical section through the longitudinal center axis of an embodiment of the mixing channel 1 according to the invention prior to insertion of a nebulizer
Figures 11B, 11C:
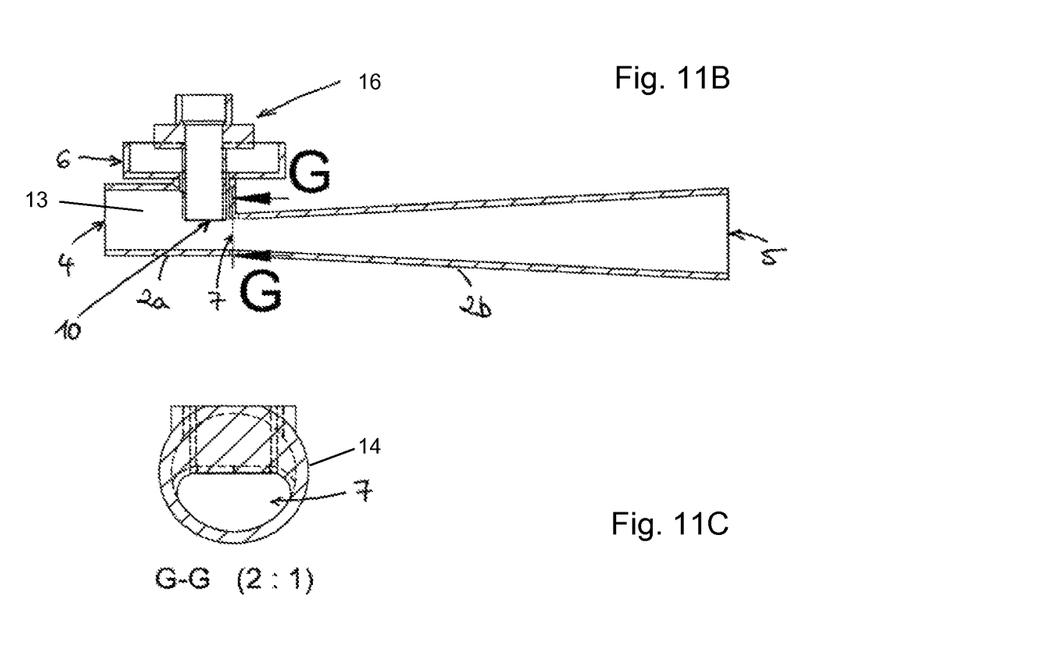
FIG. 11B shows a vertical section through the longitudinal center axis of an embodiment of the mixing channel 1 according to the invention with a nebulizer inserted
FIG. 11C shows an enlarged cross section of the mixing channel at the transition opening 7 between first channel portion 2a and second channel portion 2b along the line B-B depicted in FIG. 11B

FIG. 11A shows a vertical section through the longitudinal center axis of an embodiment of the mixing channel 1 according to the invention, similar to FIG. 1A, prior to insertion of a nebulizer 16 similar to that of FIG. 9. The mixing channel 1 comprises a first channel portion 2a, or mixing chamber 13, confined by a substantially cylindrical or cylindroidal wall (14), with an inlet opening 4, a member 6 adopted to receive a detachable nebulizer 16 and its through-hole 3a; a second channel portion 2b with outlet opening 5 and a transition opening 7 at the step 18 where the cross sectional diameter of the mixing channel 1 decreases abruptly, such that the cross sectional area is smaller at the step 18 in the injection zone 3 than upstream of the injection zone 3. The nebulizer 16 is to be positioned in such a way that its downstream end 15a with the perforated membrane 10 is inserted through through-hole 3a, while the piezoelectric ring-member 9 and the ring shaped widening 11 (which holds the piezoelectric ring-member 9 in place) remain on the outside of the mixing channel 1. The upstream end 15b of the nebulizer 16 is open and connectable to a liquid reservoir. Optionally, the nebulizer 16 may be fixed within reservoir member 25 (not shown), so that proper insertion of the nebulizer is assured by the correct assembly of reservoir member 25 onto the inhalation device as depicted in FIGS. 7 and 8.

FIG. 11B shows a vertical section through the longitudinal center axis of an embodiment of the mixing channel 1 according to the invention as depicted in FIG. 11A, now with the nebulizer 16 inserted and positioned such that the downstream part 15a of the nebulizer 16 with the perforated membrane 10 is positioned approximately flush with the upper part of the inner surface of the wall of the mixing channel 1 downstream of the injection zone 3. In other words, the end of the downstream part 15a of the nebulizer 16 is flush with the step 18.

FIG. 11C shows an enlarged cross section of the mixing channel at the transition opening 7 between first channel portion 2a and second channel portion 2b along the line B-B depicted in FIG. 11B.

Figure 12:
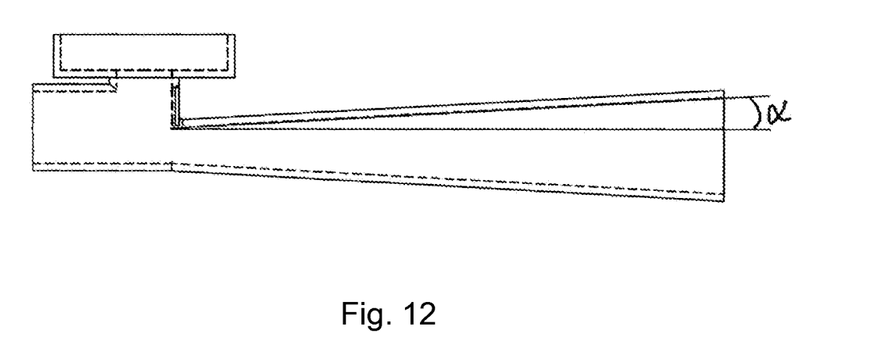
FIG. 12 shows the angle α between the center axis of the second channel portion and one exemplary tangential plane on the inner surface of the second channel portion, i.e., the line of the tangential plane which is also part of a longitudinal section Embodiments of the invention are explained below with the help of FIGS. 1A to 9, FIGS. 11 and 12.

FIG. 12 shows the angle α between the center axis of the second channel portion 2b and an exemplary tangential plane on the inner surface (or, in this case, the line at the intersection of a vertical longitudinal section and the inner surface) of the second channel portion 2b.

EXAMPLE 1

Five prototype mixing channels (nos. 1 to 5) with different geometries were designed and prepared. The second channel portions were approx. 80 mm long and slightly tapered, i.e. shaped as truncated, roughly circular, cones. The prototypes differed with respect to the diameter of the inlet opening and the opening angle of the cone (which is twice the angle between the center axis of the second channel portion and any tangential plane on the inner surface of the second channel portion). In prototypes nos. 1 to 3, the opening angles increased from a smaller angle at the proximal (or upstream) end to a larger angle at the distal (or downstream) end of the second channel portion. The dimensions of the transition opening at the step between first and second mixing channel portion were selected according to the inlet diameter, in that the radius was not changed but the shape was altered from circular to semi-circular with rounded edges, as depicted in FIG. 11C. The respective parameters are given in table 1.

TABLE 1

| | Mixing channel no. | | | | |
|---|---|---|---|---|---|
| | 1 | 2 | 3 | 4 | 5 |
| Inlet diameter (mm) | 10 | 9 | 8 | 9 | 9 |
| Opening angle | 5° to 6° | 5° to 6° | 5° to 6° | 5° | 6° |

Two aerosol generators (A and B) as described in US 2010/0044460 A1 were used to aerosolise isotonic saline solution (0.9%) in pulses of 5 seconds of aerosolization time followed by pauses of 5 seconds. The experiments were conducted first without any mixing channel, and subsequently with each of the five mixing channels at a flow rate of 15 L/min. In each configuration, the aerosol droplet size distribution was determined using laser diffraction. The volume median diameters (VMD) and the geometric standard deviations (GSD) are given in table 2 for aerosol generator A and in table 3 for aerosol generator B.

TABLE 2

| | Mixing channel no. | | | | | |
|---|---|---|---|---|---|---|
| | None | 1 | 2 | 3 | 4 | 5 |
| VMD (pulsed mode) | 5.3 | 5.0 | 5.2 | 4.9 | 5.0 | 5.1 |
| GSD (pulsed mode) | 6.4 | 1.6 | 1.6 | 1.6 | 1.6 | 1.6 |

TABLE 3

| | Mixing channel no. | | | | | |
|---|---|---|---|---|---|---|
| | None | 1 | 2 | 3 | 4 | 5 |
| VMD (pulsed mode) | 5.5 | 4.7 | 4.8 | 4.7 | 4.7 | 4.7 |
| GSD (pulsed mode) | 3.6 | 1.6 | 1.6 | 1.6 | 1.6 | 1.6 |

In result, a remarkable and—especially in its magnitude completely unexpected—effect of all tested mixing channels was observed in that the geometric standard deviation, i.e. the polydispersity of the aerosol droplets, was dramatically reduced from 6.4 or 3.6 to 1.6, indicating that these aerosol generators, which emit substantially heterogeneous aerosols without any mixing channel can, by means of the mixing channel of the invention, be configured to deliver substantially homogeneous aerosols.

EXAMPLE 2

Using the same five prototype mixing channels as in example 1 and aerosol generator A, and an additional mixing channel (no. 6, with an inlet diameter of 10 mm and a constant opening angle of 6°), the deposition of the aerosolised isotonic saline solution (0.9%) within the mixing channels at a flow rate of 15 L/min was evaluated. An exactly measured quantity of isotonic saline solution (i.e., $NaCl_{total}$) was filled into the reservoir of the aerosol generator and aerosolised while a breathing pump (ASL 5000 by IngMar Medical) simulated 20 breathing manoeuvres. Subsequently, the reservoir and the mixing channel were rinsed with distilled water and their sodium chloride content measured conductometrically. Deposition within the mixing channel ($NaCl_{deposited}$) was calculated in percent based on the emitted dose ($NaCl_{emitted} = NaCl_{total} - NaCl_{left\ in\ reservoir}$). The results are given in Table 4.

TABLE 4

|  | Mixing channel no. | | | | | |
| --- | --- | --- | --- | --- | --- | --- |
|  | 1 | 2 | 3 | 4 | 5 | 6 |
| Inlet diameter (mm) | 10 | 9 | 8 | 9 | 9 | 10 |
| Opening angle | 5° to 6° | 5° to 6° | 5° to 6° | 5° | 6° | 6° |
| Deposition (% of emitted dose) | 9.7 | 16.7 | 27.2 | 19.2 | 10.9 | 10.3 |

In all cases, an acceptable low degree of deposition in the mixing channel was observed. This is remarkable as the nebulizer itself had not been especially adapted to, or optimised for, the inhalation device or the mixing channel, which is normally required.

A particularly low aerosol deposition in the device was found for an inlet diameter of 9 or 10 mm and an opening angle of 6°, or from 5° to 6°.

These experiments demonstrate the effectiveness of the mixing channels in deflecting the vast majority of the aerosol droplets emitted by the nebulizer, such that they can be delivered through the mouthpiece to the user. A relatively small fraction of droplets—probably those having the relatively largest diameter—impacted within the device. Their removal may contribute to the reduction of the geometric standard deviation of the aerosol droplet diameter, as observed in Example 1.

In addition, computational flow simulations of the prototype mixing channels indicated that the length of the second mixing channel portion of approx. 80 mm is efficient in slowing down the velocity of the aerosol droplets to a value very similar to the velocity upstream of the injection zone and thus suitable for inhalation into the deeper lung areas without impaction in the mouth and/or throat region.

The computational flow simulations of the prototype mixing channels further indicated that these effects may be achieved by means of the step in the mixing channel (i.e. an abrupt decrease of the effective cross sectional area), e.g. through an abrupt increase in air velocity caused by the step, without interfering with a laminar flow.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A mixing channel for an inhalation device, comprising a first channel portion, comprising
   an inlet opening, and
   an injection zone;
a second channel portion, comprising
   an outlet opening,
wherein the injection zone is located between the inlet opening and the outlet opening, wherein a portion of the mixing channel proximate to the inlet opening from the injection zone is upstream, and wherein a portion of the mixing channel proximate to the outlet opening from the injection zone is downstream; and
a step located within the injection zone or at a downstream end of the injection zone,
wherein the step is not a baffle-type wall, wherein the injection zone has a longitudinal center axis, wherein the injection zone comprises a nebulizer, wherein an effective cross sectional area of the mixing channel in a plane perpendicular to the longitudinal center axis decreases abruptly in the direction of air flow within or at the downstream end of the injection zone as a result of the step, such that said effective cross sectional area is smaller in the injection zone or at the downstream end of the injection zone than upstream of the injection zone, wherein an inner surface of a wall of the mixing channel forms a step-free transition between a downstream end of the first channel portion and an upstream end of the second channel portion on the side opposite to the nebulizer and does not contribute to the step in the mixing channel, wherein an opening angle of the second channel portion immediately downstream of the step is constant, and wherein the nebulizer is built-in or detachable, and wherein the step obstructs about 50% of the cross-section in the plane perpendicular to the longitudinal center axis of the injection zone.

2. The mixing channel of claim 1, wherein the nebulizer extends from a lateral position relative to the longitudinal center axis of the injection zone and protrudes into the injection zone to form the step.

3. The mixing channel of claim 1, wherein the nebulizer is positioned such as to emit an aerosol at the longitudinal center axis of the injection zone, or near and towards the longitudinal center axis of the injection zone, at an angle of 90° or an angle from 45° to 135° with respect to the longitudinal center axis of the injection zone.

4. The mixing channel of claim 1, wherein the opening angle of the second channel portion immediately downstream of the step is not more than 8°.

5. The mixing channel of claim 1, wherein the inlet opening of the mixing channel forms an inlet opening of the inhalation device, or is connectable with an inlet channel of the inhalation device.

6. The mixing channel of claim 1, further comprising a filter positioned upstream of the injection zone.

7. The mixing channel of claim 1, wherein the inner surface of the wall of the mixing channel is at least partially coated with a layer of a biocompatible material.

8. The mixing channel of claim 1, wherein the nebulizer is a vibrating mesh nebulizer.

9. The mixing channel of claim 8, wherein the nebulizer comprises a main member, a ring member made of piezoelectric material, and a perforated membrane, wherein the main member comprises a tubular portion comprising an outer area exhibiting a ring-shaped widening onto which the ring member is attached such that the main member extends through the ring member, and the perforated membrane being connected into or onto a front part of the main member; and the main member being connectable with a liquid drug reservoir.

10. The mixing channel of claim 9, wherein the perforated membrane of the nebulizer is flush with a part of the inner surface of the wall of the mixing channel downstream of the injection zone.

11. The mixing channel of claim 9, wherein the perforated membrane of the nebulizer is adjacent to the step, and wherein the nebulizer is upstream of the step.

12. An inhalation device comprising the mixing channel of claim 1.

13. The mixing channel of claim 1, wherein the injection zone is where the injection of a nascent aerosol from the nebulizer occurs.

14. The mixing channel of claim 1, wherein the injection zone is where an aerosol emitted from the nebulizer is initially mixed with air.

15. A mixing chamber for an inhalation device having a substantially cylindrical or cylindroidal wall and a longitudinal center axis, comprising an inlet opening at an upstream end of the mixing chamber, a mixing chamber outlet opening at a downstream end of the mixing chamber, an injection zone for aerosol, a built-in or detachable nebulizer extending from a top of the mixing chamber such as to protrude into the injection zone and to emit the aerosol at or near the longitudinal center axis of the mixing chamber at an angle of 90° or an angle from 45° to 135° with respect to the longitudinal center axis of the mixing chamber, wherein the mixing chamber outlet opening is in a plane perpendicular to the longitudinal center axis of the mixing chamber, and wherein the mixing chamber outlet opening is entirely positioned between the longitudinal center axis of the mixing chamber and the substantially cylindrical or cylindroidal wall of the mixing chamber opposite of the position from which the built-in or detachable nebulizer extends into the mixing chamber.

16. An inhalation device comprising the mixing chamber of claim 15.

17. The mixing chamber of claim 15, wherein the mixing chamber further comprises a wall that is arranged on a cross sectional plane orthogonal to the longitudinal center axis of the mixing chamber, wherein said wall covers about 50% of the cross sectional area at the downstream end of the mixing chamber on the same side as the built-in or detachable nebulizer.

18. A mixing channel for an inhalation device, comprising
a first channel portion comprising an inlet opening and an injection zone,
a second channel portion comprising an outlet opening, wherein the injection zone is located between the inlet opening and the outlet opening, wherein a portion of the mixing channel proximate to the inlet opening from the injection zone is upstream, and wherein a portion of the mixing channel proximate to the outlet opening from the injection zone is downstream, and
a step located within the injection zone or at a downstream end of the injection zone, wherein the step is not a baffle-type wall, wherein the injection zone has a longitudinal center axis, wherein the injection zone comprises a member adapted to receive a detachable nebulizer, wherein an effective cross sectional area of the mixing channel in a plane perpendicular to the longitudinal center axis decreases abruptly in the direction of air flow within or at the downstream end of the injection zone as a result of the step, such that said effective cross sectional area is smaller in the injection zone or at the downstream end of the injection zone than upstream of the injection zone, wherein an inner surface of a wall of the mixing channel forms a step-free transition between a downstream end of the first channel portion and an upstream end of the second channel portion on the side opposite to the nebulizer and does not contribute to the step in the mixing channel, wherein an opening angle of the second channel portion immediately downstream of the step is constant, and wherein the step obstructs about 50% of the cross-section in the plane perpendicular to the longitudinal center axis of the injection zone.

19. The mixing channel of claim 18, further comprising the detachable nebulizer, wherein upon the detachable nebulizer being received in said member adapted to receive the detachable nebulizer, the detachable nebulizer extends from a lateral position relative to the longitudinal center axis of the injection zone and protrudes into the injection zone to form the step.

20. The mixing channel of claim 18, wherein the opening angle of the second channel portion immediately downstream of the step is not more than 8°.

21. The mixing channel of claim 18, wherein the inlet opening of the mixing channel forms an inlet opening of the inhalation device, or is connectable with an inlet channel of the inhalation device.

22. The mixing channel of claim 18, comprising a filter positioned upstream of the injection zone.

23. The mixing channel of claim 18, wherein the inner surface of the wall of the mixing channel is at least partially coated with a layer of a biocompatible material.

24. The mixing channel of claim 18, wherein the injection zone is where the injection of a nascent aerosol from the nebulizer occurs.

25. The mixing channel of claim 18, wherein the injection zone is where an aerosol emitted from the nebulizer is initially mixed with air.

26. The mixing channel of claim 18, wherein the step is downstream of the member adapted to receive the detachable nebulizer.

* * * * *